United States Patent [19]

Franck et al.

[11] Patent Number: 5,124,449
[45] Date of Patent: Jun. 23, 1992

[54] AZAPORPHYRIN DERIVATIVES

[75] Inventors: Burchard Franck, Muenster; Hartmann Koenig, Limburgerhof; Christian Eickmeier; Michael Voelker, both of Muenster; Thomas Wessel, Nottuln, all of Fed. Rep. of Germany

[73] Assignee: BASF Aktiengesellschaft, Ludwigshafen, Fed. Rep. of Germany

[21] Appl. No.: 748,867

[22] Filed: Aug. 23, 1991

[30] Foreign Application Priority Data

Sep. 20, 1990 [DE] Fed. Rep. of Germany ....... 4029768
Mar. 20, 1991 [DE] Fed. Rep. of Germany ....... 4109085

[51] Int. Cl.⁵ .......................................... C07D 487/22
[52] U.S. Cl. .................................. 540/472; 548/455; 548/465; 548/505; 548/506; 548/518
[58] Field of Search ......................................... 540/472

[56] References Cited

U.S. PATENT DOCUMENTS 4,657,554  4/1987  Reinert et al. ............... 540/121
4,798,891  1/1989  Franck et al. ............... 540/472

OTHER PUBLICATIONS

Ann. Chem., 1976, pp. 1637–1658, J. Engel, et al., "Synthese Neuer Biladien-a,c-Derivate und Ihre Cyclisierung zu Uroporphyrin-III-, 12-Descarboxyuroporhyrin-III- und Phyriaporphyrin-III-Methylestern¹".
The Journal of Organic Chemistry, vol. 41, No. 17, 1976, pp. 2826–2835, J. B. Paine III¹, et al., "Pyrrole Chemistry. The Cyanovinyl Aldehyde Protecting Groups".

Primary Examiner—John M. Ford
Assistant Examiner—Jyothsna Venkat
Attorney, Agent, or Firm—Oblon, Spivak, McClelland, Maier & Neustadt

[57] ABSTRACT

Azaporphyrin derivatives of the formula

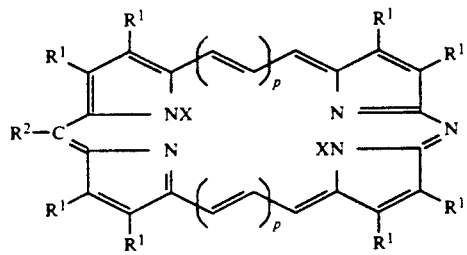

where
$R^1$ and $R^2$ are each, independently of one another, hydrogen, unsubstituted or substituted $C_1$–$C_{20}$-alkyl, $C_5$–$C_7$-cycloalkyl or unsubstituted or substituted phenyl, or two adjacent $R^1$ radicals form, together with the carbon atoms to which they are bonded, an unsaturated or aromatic 5- to 7-membered carbocyclic ring,
X are each hydrogen or $C_1$–$C_4$-alkyl and
p are each 1 or 2, and
biladienes of the formula

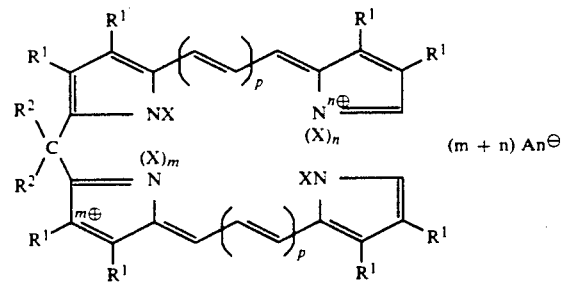

where $R^1$, $R^2$, X and p each have the abovementioned meanings, m and n are each 0 or 1 and $An^\ominus$ is an anion, as intermediates therefor, are used for preparing vinylogous porphyrin derivatives.

2 Claims, No Drawings

AZAPORPHYRIN DERIVATIVES

The present invention relates to novel azaporphyrin derivatives of the formula I

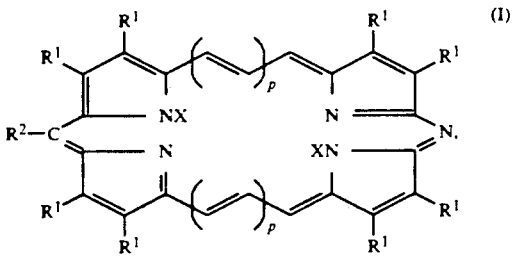

where
R$^1$ and R$^2$ are each, independently of one another, hydrogen, unsubstituted or substituted C$_1$-C$_{20}$-alkyl, C$_5$-C$_7$-cycloalkyl or unsubstituted or substituted phenyl, or two adjacent R$^1$ radicals form, together with the carbon atoms to which they are bonded, an unsaturated or aromatic 5- to 7-membered carbocyclic ring,
the X radicals are each, independently of one another, hydrogen or C$_1$-C$_4$-alkyl, and
p are each, independently of one another, 1 or 2.

The present invention furthermore relates to novel biladienes of the formula II

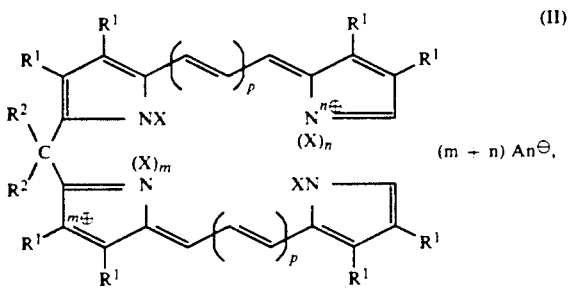

where
R$^1$ and R$^2$ are each, independently of one another, hydrogen, unsubstituted or substituted C$_1$-C$_{20}$-alkyl, C$_5$-C$_7$-cycloalkyl or unsubstituted or substituted phenyl, or two adjacent R$^1$ radicals form, together with the carbon atoms to which they are bonded, an unsaturated or aromatic 5- to 7-membered carbocyclic ring,
the X radicals are each, independently of one another, hydrogen or C$_1$-C$_4$-alkyl,
m and n are each, independently of one another, 0 or 1, p are each, independently of one another, 1 or 2 and An$^\ominus$ is an anion.

U.S. Pat. No. 4,798,891 discloses porphyrin derivatives which, apart from the four pyrrole nitrogens, contain no further hetero atoms in the prophyrin ring.

Ann. Chem. (1976) 1637-1658 has furthermore disclosed biladienes. However, it has emerged that the components described therein are unsuitable for preparing vinylogous porphyrin compounds.

It is an object of the present invention to provide novel porphyrin derivatives which have an additional nitrogen in the porphyrin ring.

It is a further object of the present invention to provide novel biladiene derivatives which can be used to synthesize vinylogous porphyrin compounds and azaporphyrin derivatives in an advantageous manner.

We have found that these objects are achieved by the azaporphyrin derivatives of the formula I defined at the outset and the biladiene derivatives of the formula II.

All the alkyl and alkylene groups in the abovementioned formulae I and II can be either straight-chain or branched.

Examples of suitable substituents for substituted alkyl in the abovementioned formulae I and II are phenyl and C$_1$-C$_{12}$-alkoxycarbonyl.

Examples of suitable substituents for substituted phenyl in the abovementioned formulae I and II are halogen, especially chlorine or bromine, cyano, C$_1$-C$_4$-alkyl, C$_1$-C$_4$-alkoxy, nitro or C$_1$-C$_4$-alkoxycarbonyl.

Examples of R$^1$ and R$^2$ are methyl, ethyl, propyl, isopropyl, butyl, isobutyl, sec-butyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl, eicosyl (the names isooctyl, isononyl, isodecyl and isotridecyl are trivial names derived from the alcohols produced in the oxo synthesis, cf. Ullmanns Encyklopädie der technischen Chemie, 4th Edition, volume 7, pages 215 to 217, and volume 11, pages 435 and 436), benzyl, 1- or 2-phenylethyl, methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, 2-methoxycarbonylethyl, 2-ethoxycarbonylethyl, 2-propoxycarbonylethyl, 2-isopropoxycarbonylethyl, 2-butoxycarbonylethyl, 2- or 3-methoxycarbonylpropyl, 2- or 3-ethoxycarbonylpropyl, 2- or 4-methoxycarbonylbutyl, 2- or 4-ethoxycarbonylbutyl, cyclopentyl, cyclohexyl, methylcyclohexyl, cycloheptyl, phenyl, 2-, 3- or 4-chlorophenyl, 2-, 3- or 4-bromophenyl, 2,4-dichlorophenyl, 2-, 3- or 4-cyanophenyl, 2-, 3- or 4-methylphenyl, 2,4-dimethylphenyl, 2-, 3- or 4-methoxyphenyl or 2,4-dimethoxyphenyl.

When two adjacent R$^1$ radicals form, together with the carbon atoms to which they are bonded, an unsaturated or aromatic 5- to 7-membered carbocyclic ring, suitable examples are the cyclopentene, cyclopentadiene, cyclohexene, cyclohexadiene, benzene, cycloheptene, cycloheptadiene and cycloheptatriene rings. Each of these rings may be substituted by C$_1$-C$_4$-alkyl.

An$^\ominus$ in formula I is an anion. Suitable anions are inorganic or organic, e.g. halides such as chloride, bromide or iodide, sulfate, perchlorate, phosphate, tetrafluoroborate, trichlorozincate, methanesulfonate, benzene sulfonate, 4-methylbenzenesulfonate, acetate, lactate, salicylate and tetraphenylborate.

Preferred azaporphyrin derivatives of the formula one another, hydrogen, unsubstituted or phenyl- or C$_1$-C$_4$-alkoxycarbonyl-substituetd C$_1$-C$_4$-alkyl or phenyl, and the X radicals are each, independently of one another, hydrogen, methyl or ethyl.

Furthermore, preferred biladienes of the formula II are those in which R$^1$ and R$^2$ are each, independently of one another, hydrogen, unsubstituted or phenyl- or C$_1$-C$_4$-alkoxycarbonyl-substituted C$_1$-C$_4$-alkyl or phenyl, and the X radicals are each, independently of one another, hydrogen, methyl or ethyl, and m, n, p and An$^\ominus$ each have the abovementioned meanings.

The novel azaporphyrin derivatives of the formula I can be obtained by reacting the biladiene derivatives of the formula II with ammonia, followed by oxidation.

The novel biladienes of the formula II can be obtained by conventional methods. For example, dipyrrylmethanes of the formula IV

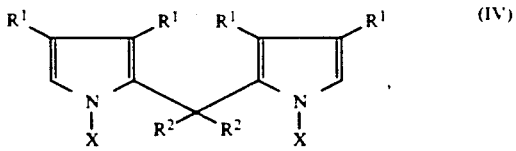

where $R^1$, $R^2$ and X each have the abovementioned meanings, can be reacted with aldehydes of the formula V

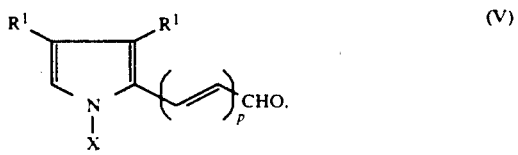

where $R^1$, X and p each have the abovementioned meanings, in the presence of an acid condensing agent, e.g. hydrobromic acid.

The dipyrrylmethanes of the formula IV and the aldehydes of the formula V are known or can be obtained by conventional methods as are described, for example, in J. Org. Chem. 41 (1976) 2826–2835 and in U.S. Pat. No. 4,798,901.

The novel biladienes of the formula II are valuable intermediates for synthesizing vinylogous porphyrin derivatives of the formula III

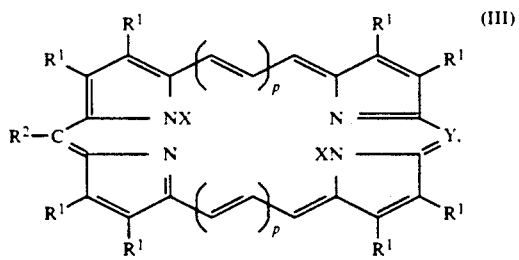

where Y is nitrogen or $CR^2$, and $R^1$, $R^2$, X and p each have the abovementioned meanings.

The compounds of the formula III (where $Y=CR^2$) are disclosed in U.S. Pat. No. 4,798,891.

The biladienes of the formula II can be converted into the porphyrins III (where $Y=CR^2$) by reaction with aldehyde of the formula VI $R^2$—CHO (VI).

where $R^2$ has the abovementioned meanings, in the presence of an acid condensing agent, e.g., hydrobromic acid, and subsequent oxidation.

The azaporphyrins of the formula I according to the invention can be used, for example, as sensitizers for photochemical reactions, in optical memories or in photomedicine, e.g., in photodynamic tumor therapy.

The examples illustrate the invention.

EXAMPLE 1

355 mg (2.00 mmol) of 3-(3,4-diethyl-2-pyrryl)acrolein and 258 mg (1.00 mmol) of bis(3,4-diethyl-2-pyrryl)methane were dissolved in 7 ml of methanol and cooled to $-15°$ C. Then, while stirring vigorously at this temperature, 0.4 ml of 62% by weight hydrobromic acid was added dropwise and the mixtrue was then stirred for 5 minutes. The deep green precipitate was filtered off and washed with a little ice-cold methanol and with n-hexane. High-vacuum drying at 40 C. resulted in 601 mg (81%) of the biladiene of the formula

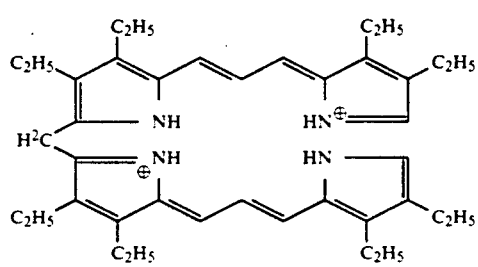

in the form of fine dark green needles. Melting point: decomposition without melting above about 160° C.

$^1$H NMR (300 MHz, $CD_2Cl_2$): $\delta=0.75$ (t, J=7.4 Hz, 6H, $CH_2C\underline{H}_3$), 1.15–1.23 (m, 18H, $CH_2C\underline{H}_3$), 2.46–2.57, 2.59–2.71 (2m, each 8H, $C\underline{H}_2CH_3$), 4.62 (s, 2H, bridge $CH_2$), 7.43–7.50 (m, 6H, $C\underline{H}$=CHC$\underline{H}$and pyrrole α-H), 9.03 (t,J=13.6 Hz, 2H, CH=$C\underline{H}$CH), 11.80, 1284 (2 br. s, each 2H, NH).

MS (70 eV): m/z (%)=578 (20) [M-2 Br], 577 (70) [M-2 Br—H], 576 (27) [M—H], 576 (27) [M—HBr] 547 (6) [576—$C_2H_5$], 453 (6) [576-monopyrrole unit].

IR (KBr): $\nu=2960$, 2920, 2860 cm$^{-1}$ (w, CH), 1570 cm$^{-1}$ (s, conjug. C=C).

UV/VIS ($CHCl_3$): $\lambda_{max}$ (1 g $\epsilon$)=657 nm (5.267), 547 nm (4.664), 504 nm (4.390).

$C_{39}H_{54}Br_2N_4$(738.7) Calc. C 63.41, H 7.37, N 7.58, Br 21.63, Found C 63.30, H7.50, N 7.56, Br 21.53.

EXAMPLE 2

280 mg (1.37 mmol) of 5-(3,4-diethyl-2-pyrryl)-2,4-pentadienal and 180 mg (0.69 mmol) of bis(3,4-diethyl-2-pyrryl)methane were dissolved in 7 ml of methanol and cooled to $-15°$ C. While stirring vigorously at this temperature, 0.3 ml of 62% by weight hydrobromic acid was added dropwise and the mixture was then stirred for 10 minutes. The olive green precipitate was filtered off with suction and washed with a little ice-cold methanol and with n-pentane. Further product crystallized from the mother liquor at $-30°$ C. Drying under oil pump vacuum resulted in the analytically pure biladiene salt of the formula

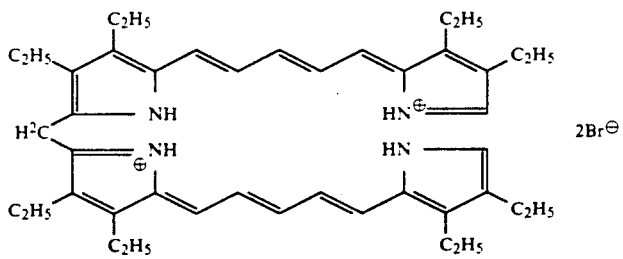

as a dark green powder which gave a deep blue solution.

Yield: 463 mg (40.3%)

Melting Point: Decomposition without melting above about 120° C.

TLC (dichloromethane/methanol 20:1 v/v): $R_f = 0.60$ $^1$H NMR (300 MHz, [D$_6$]DMSO): $\delta = 1.02-1.21$ (m, 24H, CH$_2$C$\underline{\text{H}}_3$), 2.33-2.41, 2.52-2.60 (2 m, each 8H, C$\underline{\text{H}}_2$CH$_3$), 5.56, 5.61 (2 br. s, 2H, bridge CH$_2$), 6.75-7.27 (m, 12H, CH=CH—CH=CH—CH and pyrrole α-H), 11.06, 11.18 (2 br. s, each 2H, NH).

MS (70 eV): m/z (%) = 6.29(20) [M-2 Br—H], 628 (24) [M-2 HBr], 599 (6) [628—C$_2$H$_5$, 491 (30) [628-monopyrrole unit].

IR (KBr): $\nu = 2980$, 2910, 2860 cm$^{-1}$ (w, CH), 1570 (s. conj. C=C).

UV/VIS (CH$_2$Cl$_2$): $\epsilon_{max}$ (1 g $\epsilon$) = 785 nm (4.340), 621 (5.544), 410 (4.237).

C$_{43}$H$_{58}$Br$_2$N$_4$ (b 790.8) Calc. C 62.31, H 7.39, N 7.09, Br 20.21, Found C 65.30, H 7.47, N 7.06, Br 20.22.

EXAMPLE 3

0.25 mmol of the biladiene salt of the formula

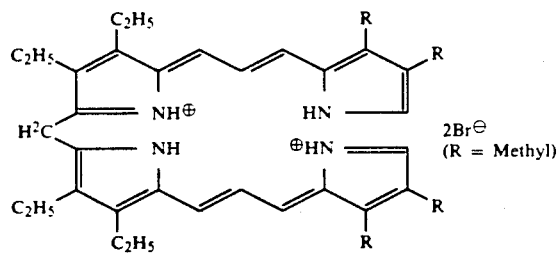

was dissolved in 90 ml of methanol. 3.5 ml of 25% by weight aqueous ammonia solution were added to the deep blue solution. The solution became yellowish green and 284 mg (1.25 mmol) of 2,3-dichloro-5,6-dicyano-1,4-benzoquinone dissolved in 15 ml of methanol were added and the mixture was stirred at room temperature for 1 hour.

It was then left to stand in an ice bath for 1 hour in order to complete the precipitation, and was then filtered. The residue on the filter was taken up in dichloromethane/methanol (20:1 v/v) and loaded, together with the insoluble residue, onto a silica gel column and chromatographed (Merck silica gel 60, particle size 0.063–0.200 mm, dichloromethane/methanol 20:1 v/v). Evaporation of the green eluate fractions under reduced pressure resulted in an azaporphyrin of the formula

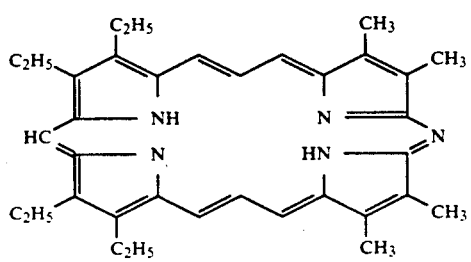

as bluish green shiny color lake in analytically pure form.

Yield: 23 mg (17%); decomposition point: 320°–330° C.

FT—IR (KBr): $\nu = 3437$ cm$^{-1}$ (s, br., NH), 3034 (w, =CH), 2966, 2928, 2870 (s, CH).

$^1$H NMR (300 MHz, CDCl$_3$ + 1% TFA-d$_1$): $\delta = -7.47$ (t, J = 13.7 Hz, 2H, trimethine bridge CH=CHCH), 2.11 (t, J = 7.5 Hz, 12H, CH$_2$C$\underline{\text{H}}_3$), 3.93 (s, 6H, CH$_3$), 3.97 (s, 6H, CH$_3$), 4.48 (q, J = 7.5 Hz, 8H, C$\underline{\text{H}}_2$CH$_3$), 11.36 (s, 1H, monomethine bridge CH), 11.92, 11.99 (d, J = 13.2 Hz, 2H; d, J = 14.3 Hz, 2H; trimethine bridge CH=CHCH).

MS (70 eV): m/z (%) = 532 (22) [M$^+$+H], 531 (58) [M$^+$], 516 (19) [M$^+$—MH$_3$], 502 (21) [M$^+$—C$_2$H$_5$], 487 (15) [5.16—C$_2$H$_5$], 473 (17) [502—C$_2$H$_5$], 458 (16) [473—CH$_3$], 266 (42) [M$^+$/2].

UV/VIS (CH$_2$Cl$_2$): $\lambda_{max}$ (1 g $\epsilon$) = 451 nm (5.129), 589 (3.898), 630 (4.037), 692 (3.672), 775 (3.393).

UV/VIS (CH$_2$Cl$_2$ + 1% TFA): $\lambda_{max}$ (1 g $\epsilon$) = 451 nm (5.523), 612 (3.937), 659 (4.097), 681 (4.157), 741 (3.393).

C$_{35}$H$_{41}$N$_5$ Calc. 531.3362, Found 531.3371 (MS).

C$_{35}$H$_{41}$N$_5$·0.3 CH$_2$Cl$_2$ (557.22) Calc. C 76.09, H 7.52, N 12.57, Found C 76.43, H 7.83, N 12.41.

EXAMPLE 4

Example 4 was carried out in a similar manner to Example 3 but the ethyl compound (R = ethyl) was used as biladiene salt.

The result was 29 mg (20%) of the compound of the formula

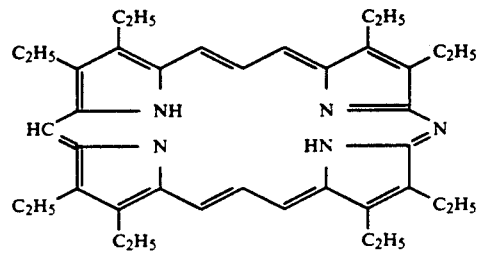

as bluish green shiny color lake. Decomposition point: 320°-330° C.

FT—IR (KBr): $\nu = 3431$ cm$^{-1}$ (s, br., NH), 3038 (w, =CH), 2963, 2930, 2869 (s, CH).

$^1$H—NMR (300 MHz, CDCl$_3$+1% TFA-d$_1$): $\delta = -7.55$ (t, J=13.7 Hz, 2H, trimethine bridge CH=CHCH), 2.12 (m$_c$, 24H, CH$_2$CH$_3$), 4.50 (m$_c$, 16H, CH$_2$CH$_3$), 11.40 (s, 1H, monomethine bridge CH), 11.96, 12.03 (d, J=13.2 Hz, 2H; d, J=14.3 Hz, 2H; trimethine bridge CH=CHCH).

MS (70 eV): m/z (%)=587 (22) [M+], 500 (18) [M+−3C$_2$H$_5$], 293 (26) [M+/2], 280 (27) [dipyrrotrimethine unit+], 249 (27) [M+/2—C$_2$H$_5$—CH$_3$], 235 (34) [M+/2—2C$_2$H$_5$].

UV/VIS (CH$_2$Cl$_2$): $\lambda_{max}$ (1 g $\epsilon$) = 450 nm (5.186), 590 (4.076), 631 (4.204), 694 (3.787), 776 (3.611).

UV/VIS (CH$_2$Cl$_2$+1% TFA): $\lambda_{max}$ (1 g $\epsilon$) = 453 nm (5.568), 614 (4.094), 660 (4.207), 682) 4.222), 743 (3.586).

C$_{39}$H$_{49}$H$_5$ Calc. 587.3988, Found 587.4000 (MS), C$_{39}$H$_{49}$N$_5$.0.1 CH$_2$Cl$_2$ )596.34) Calc. C 78.75, H 8.32, N 11.74, Found C 78.81, H 8.77, N 10.85.

EXAMPLE 5

79.5 mg (0.10 mmol) of the biladiene salt from Example 2 were dissolved in 30 ml of methanol. 2.0 ml of concentrated aqueous ammonia solution were added to the deep blue solution. After 10 minutes, 114 mg (0.50 mmol) of dichlorodicyanoquinone in 6 ml of methanol were added to this solution, and the mixture was stirred at room temperature for 1 hour. It was then left to stand at −30° C. for 1 hour, after which the greenish precipitate was filtered off with suction. The residue on the filter was taken up as far as possible in dichloromethane/methanol (20:1 v/v) and chromatographed together with the insoluble residue on a short column (dichloromethane/methanol 20:1 v/v, column diameter: 5 cm, packing height: 15 cm). Evaporation of the red eluate fractions under reduced pressure resulted in the azaporphyrin of the formula

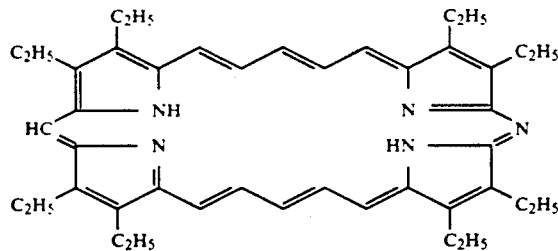

as bluish green shiny color lake.

Yield: 11.4 mg (17.9%),

Melting point: decomposition above about 215° C.

TLC (dichloromethane/methanol 20:1 v/v): R$_f$=0.23, $^1$H NMR (300 MHz, CF$_3$CO$_2$D): $\delta = -4.47$ (m$_c$, 4 h, CHCHCHCHCH), 2.15 (m$_c$, 24H, $\beta$-CH$_3$), 4.46 (m$_c$, 16H, $\overline{\beta}$-CH$_2$), 11.26 (s, 2.15 (m$_c$, 24H, $\beta$-CH$_3$), 4.46 (m$_c$, 16H, $\beta$-CH$_2$), 11.26 (s, 1H, monomethine bridge H), 11.77, 12.03 (2 d, J=12.5 Hz, 4H, CHCHCHCHCH), 12.53 (t, J=12.7 Hz, 2H, CHCHCHCHCH).

MS (70 eV): m/z (%)=641 (24) [M+2], 640 (32) [M+1), 639 (56) [M+], 624 (24) [M—CH$_3$], 10 (40) [M—C$_2$H$_5$], 320 (30) [(M+1)/2].

IR (KBr): $\nu = 3410$ cm$^{-1}$ (w, NH), 2960, 2920, 2860 (s, CH).

UV/VIS (CH$_2$Cl$_2$): $\lambda_{max}$ (1 g $\epsilon$) = 490 nm (5.229), 649 (4.445), 697 (4.181).

UV/VIS (CH$_2$Cl$_2$+1% TFA): $\lambda_{max}$ (1 g $\epsilon$) = 503 nm (5.560), 681 (4.513), 735 (4.440).

C$_{43}$H$_{53}$N$_5$ Calc. 638.4300 Found 639.4295 (MS), Calc. C 80.71, H 8.35, N 10.85.

EXAMPLE 6

73.9 mg (100 $\mu$mol) of the biladiene from Example 1 were dissolved in 40 ml of methanol, and 10 ml of 36% by weight aqueous formaldehyde solution were added. 0.5 ml of 5% by weight hydrobromic acid was added and then the mixture was refluxed for 30 minutes. It was then rapidly cooled to 20° C., a solution of 45 mg (0.2 mmol) of dichlorodicyanoquinone in 5 ml of dichloromethane was added and the mixture was stirred for 2 hours. It was then partitioned between dichloromethane and 2N sodium carbonate solution, and the aqueous phase was separated off and extracted with dichloromethane. The was separated off and extracted with dichloromethane. The combined organic phases were washed with water and dried over magnesium sulfate. After most of the solvent had been evaporated off, the residue was purified by column chromatography on silica gel using 20:1 (v/v) fractions under reduced pressure resulted in 24.4 mg (42%) of the porphyrin of the formula

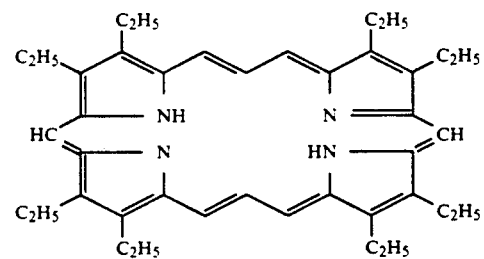

as bluish green shiny color lake. Recrystallization from chloroform/ether gave fine deep green needles. Melting point: decomposition above about 280° C. (on rapid heating).

$^1$H NMR (300 MHz, CDCl$_3$): $\delta = -8.32$ (t, J=13.3 Hz, 2H, trimethine bridge CH=CHCH), −4.73 (br. s, 2H, NH), 2.05-2.17 (m, 24H, $\beta$-$\overline{CH}_3$), 4.30-4.49 (m, 16H, $\beta$-CH$_2$), 10.48 (s, 2H, monomethine bridge CH), 11.88 (d, J=13.3 Hz, 4H, trimethine bridge CH=CHCH).

$^1$H NMR (300 MHz, CDCl$_3$+1% TFA): $\delta = -9.54$ (t, J=13.8 Hz, 2H, trimethine bridge CH=CHCH), −6.61 (br. s, 4H, NH), 2.31 (m$_c$, 24H, $\beta$-CH$_3$), 4.$\overline{85}$ (m$_c$, 16H, $\beta$-CH$_2$), 11.96 (s, 2H, monomethine bridge CH), 12.78 (d, J=13.9 Hz, 4H, trimethine bridge CH=CHCH).

MS (70 eV): m/z (%)=587 (34) [M+1], 586 (42) [M+], 571 (12) [M—CH$_3$], 557 (23) [M=C$_2$H$_5$], 513 (10) [M-2 C$_2$H$_5$—CH$_3$].

FT—IR (KBr): $\nu = 3034$ cm$^{-1}$ (w, =CH), 2963, 2928, 2868 cm$^{-1}$ (m CH), 1659, 1597 cm$^{-1}$ (w, conjug. C=C), 1055, 1013, 953 cm$^{-1}$ (s).

UV/VIS (CH$_2$Cl$_2$): $\lambda_{max}$ (1 g $\epsilon$) = 463 nm (5.622), 489 nm (4.710), 592 nm (4.035). pp UV/VIS (CH$_2$Cl$_2$+1% TFA): $\lambda_{max}$ (1 g $\epsilon$) = 434 nm (4.770), 460 nm (6.049), 607 nm (4.097), 621 nm (4.310), 678 nm (4.111), 691 nm (3.901).

C$_{40}$H$_{50}$N$_4$.0.07 CHCl$_3$ (595.2) Calc. C 80.86 H8.48 N 9.41 Found C 80.91 H 8.57 N 945

EXAMPLE 7

40.0 mg (50.6 μmol) of the biladiene salt from Example 2 were dissolved in 100ml of methanol, and 2 ml of 5% by weight hydrobromic acid were added. 10 ml of 36% by weight aqueous formaldehyde solution were added and then the solution was heated at 70° C. under an argon atmosphere for 20 minutes. The reaction mixture was then rapidly cooled to 20° C., a solution of 22 mg (0.1 mmol) of dichlorodicyanoquinone in 10 ml of dichloromethane was added, and the mixture was stirred with exclusion of light for 1.5 hours. It was partitioned between dichloromethane and 2N sodium carbonate solution, and the aqueous phase was separated off and extracted with dichloromethane. The combined organic phases were washed with water and dried over magnesium sulfate. The residue after evaporation of the solvent was purified by flash chromatography twice (column diameter: 6 cm, packing height; 30 cm, dichloromethane/acetone/methanol 8:3:1 v/v/v). Evaporation of the red eluate fractions followed by drying under oil pump vacuum resulted in the prophyrin of the formula

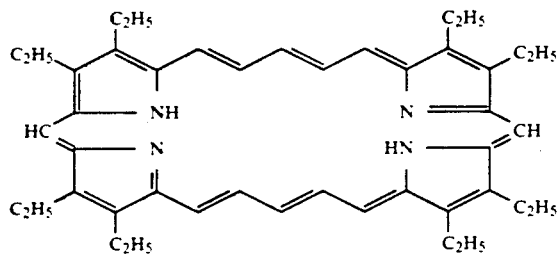

as bluish green shiny color lake (reddish violet in transmitted light).

Yield: 13.8 mg (42.7%)

Melting point: decomposition above about 180° C. (on rapid heating).

TLC (CH$_2$Cl$_2$/acetone/methanol 8:3:1 v/v/v): R$_f$=0.25

$^1$H NMR (300 MHz, [D$_6$]DMSO+1% TFA): δ= −9.79 (br. s, 4H, CHCHCHCHCH), −5.77 (br. s, 4H, NH), 2.22, 2.34, (2 t, J=7.5 Hz, each 12H, β-CH$_3$), 5.03 (m$_c$, 16 H β-CH$_2$), 12.26 (s, 2H, monomethine bridge CH), 13.51 (d, J=13.8 Hz, 4H, CHCHCHCHCH), 14.35 (t, J=7.4 Hz, 2H, CHCHCHCHCH).

MS (70 eV): m/z (%)=639 (20) [M+1], 638 (32) [M$^+$], 609 (18) [M-C$_2$H$_5$], 319 (12) [1/2 M].

IR (KBr): ν=2980, 2920, 2910 cm$^{-1}$ )(m, CH), 1590 (w, conj. C=C).

UV/VIS (CH$_2$Cl$_2$): λ$_{max}$ (1 g ε)=507 nm (5.435), 528 (5.232), 553 (4.927), 663 (4.393).

UV/VIS (CH$_2$Cl$_2$+1% TFA): λ$_{max}$ (1 g ε)=512 nm (5.841), 694 (4.608).

C$_{44}$H$_{54}$N$_4$ Calc. 638.4348, Found 638.4362 (MS). Calc. C 82.71, H 8.52, N 8.77, Found C 82.80, H 8.50, N 8.45.

EXAMPLE 8

100 mg (0.14 mmol) of the biladiene salt from Example 1 and 1.49 g (14.0 mmol) of benzaldehyde were dissolved in 40 ml of methanol, and 0.2 ml of 62% by weight hydrobromic acid was added dropwise. The reaction mixture was then refluxed for 3 hours, cooled rapidly to 20° C., and a solution of 63.0 mg (0.28 mmol) of dichlorodicyanoquinone in 5 ml of dichloromethane was added, and the mixture was stirred at room temperature for 1 hour. It was poured into 100 ml of dichloromethane and neutralized with saturated sodium bicarbonate solution. The aqueous phase was separated off and extracted with dichloromethane, and the combined organic phases were washed with water and dried over magnesium sulfate. The residue after evaporation of most of the solvent was purified by column chromatography twice on silica gel (dichloromethane/methol 25:1 v/v). Evaporation of the green eluate fraction resulted in the porphyrin of the formula

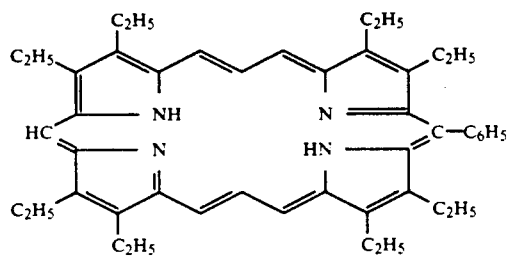

as blue metallically shiny color lake. Recrystallization from chloroform/ether resulted in fine dark green needles.

Yield: 52.3 (56%).

Melting point: decomposition without melting $^1$H NMR (300 MHz, CDCl$_3$+1% TFA): δ= −7.94 (t, J=13.5 Hz, 13.5 Hz, 2H, trimethine bridge CH=CHCH), −525 and −4.35 (2 br, s, each 2H, NH), 0.68 (t, J=7.5 Hz, 6H, CH$_2$CH$_3$), 1.66 (t, J=7.5 Hz, 6H, CH$_2$CH$_3$), 2.20 (t, J=7.5 Hz, 12H, CH$_2$CH$_3$), 2.89 (q, J=7.5 Hz, 4H, CH$_2$CH$_3$), 4.16 (q, J=7.5 H$_3$, 4H, CH$_2$CH$_3$), 4.56 (q, J=7.5 H$_3$, 8H, CH$_2$CH$_3$), 8.05 (m, 3H, phenyl-H, meta and para to porphyrin), 8.74 (d, J=6.9 Hz, 2H, phenyl-H, ortho to porphyrin), 11.07 (s, 1H, monomethine bridge CH), 12.17 and 12.24 (2 d, J=13.5 Hz, each 2H, trimethine bridge CH=CHCH).

MS (EI, 70 eV): m/z (%)=662 (52) [M$^+$], 647 (22) [M$^+$—CH$_3$], 633 (22) [M$^+$—C$_2$H$_5$], 603 (20) [M$^+$—C$_2$H$_5$—2CH$_3$], 588 (12) [M$^+$—C$_2$H$_5$—CCH$_3$].

IR (KBr): ν=3034 cm$^{-1}$ )w, =CH), 2963, 2930 and 2870 (m, CH), 1660 and 1600 (w, conjug. C=C), 1055, 1013, 953 (s).

UV/VIS (CH$_2$Cl$_2$): λ$_{max}$ (1 g ε)=470 nm (5.359), 601 (4.167).

UV/VIS (CH$_2$Cl$_2$+1% TFA): λ$_{max}$ (1 g ε)=474 nm (5.670), 638 (4.209), 690 (3.991).

C$_{45}$H$_{54}$N$_4$.0.12 CHCl$_3$ (677.3) Calc. C 81.78, H 8.05, N 8.27, Found C 81.58, H 8.16, N 8.21.

EXAMPLE 9

Example 9 was carried out in a similar manner to Example 8 but 2.12 g (0.14 mmol) of 3-nitrobenzaldehyde were used in place of benzaldehyde.

The result was 19.1 mg (19%) of the porphyrin of the formula

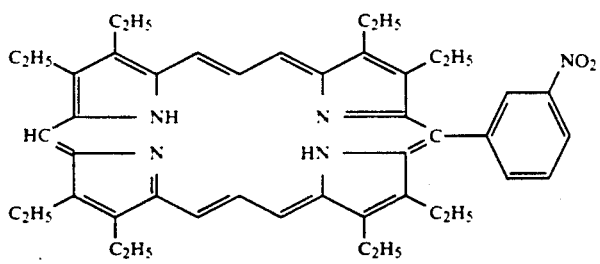

Melting point: decomposition without melting $^1$H NMR (300 MHz, CDCl$_3$+1T TFA ppm): δ = −8.03 (t, J=13.5 Hz, 2H, trimethine bridge CH=CHCH), −5.25 and −4.35 (2 br, s, each 2H, NH), 0.72 (t, J=7.5 Hz, 6H, CH$_2$CH$_3$), 1.65 (t, J=7.5 Hz, 6H, CH$_2$CH$_3$), 2.20 (t, J=7.5 Hz, 12 H, CH$_2$CH$_3$), 2.85 (q, J=7.5 Hz, 4H, CH$_2$CH$_3$), 4.19 (q, J=7.5 Hz, 4H, CH$_2$CH$_3$), 4.58 (q, J=7.5 Hz, 8 H, CH$_2$CH$_3$), 8.27 (t, J=8.1 Hz, 1H, phenyl-H, meta to porphyrin), 9.00 (d, J=9.3 Hz, 1H, phenyl-H, para to porphyrin), 9.17 (d, J=7.6 Hz, 1H, phenyl-H ortho to porphyrin), 9.67 (s, 1H, phenyl-H, ortho to porphyrin), 11.15 (s, 1H, monomethine bridge CH), 12.24 and 13.20 (2 d, J=14.0 Hz, each 2 H, trimethine bridge CH=CHCH).

MS (EI, 70 eV): m/z (%)=707 (38) [M$^+$], 692 (20) [M$^+$—CH$_3$], 678 (32) [M$^-$—C$_2$H$_5$], 663 (16) [M$^-$—C$_2$H$_5$—CH$_3$].

IR (KBr): ν=3035 c$^{-1}$ (w, =CH), 2963, 2930 and 2870 (m, CH), 1660 and 1600 (w, conjug. C=C), 1530 and 1346 (w, NO), 1055, 1013, 953 (s).

UV/VIS (CH$_2$Cl$_2$): λ$_{max}$ (1 g ε)=477 nm (5.682), 639 (4.350), 692 (4.194).

UV/VIS (CH$_2$Cl$_2$+1% TFA): λ$_{max}$ (1 g ε)=474 nm (5.712), 639 (4.630), 691 (4.194).

C$_{46}$H$_{53}$N$_5$O$_2$.0.03 CHCl$_3$ (717.2) Calc. C 77.06, H 7.47, N 9.76, Found C 77.00, H 7.77, N 9.70.

EXAMPLE 10

Example 10 was carried out in a similar manner to Example 8 but 2.30 g (0.14 mmol) of methyl 4-formylbenzoate were used in place of benzaldehyde.

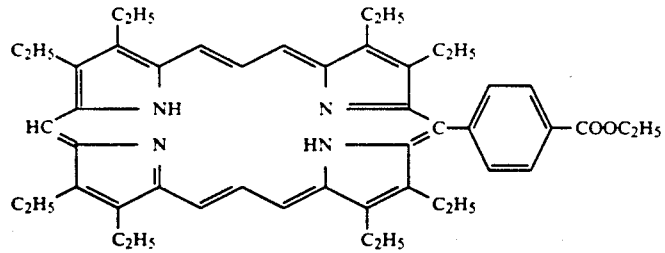

were obtained.

Melting point: decomposition melting $^1$H NMR (300 MHz, CDCl$_3$+1% TFA, ppm): δ = −8.00 (t, J=13.5 Hz, 2 H, trimethine bridge CH=CHCH), −5.25 and −4.35 (2 br, s, each 2H, NH), 0.66 (t, J=7.5 Hz, 6H, CH$_2$CH$_3$), 1.66 (t, J=7.5 Hz, 6H, CH$_2$CH$_3$), 2.19 (t, J=7.5 Hz, 12H, CH$_2$CH$_3$), 2.87 (q, J=7.5 Hz, 4H, CH$_2$CH$_3$), 4.15 (q, J=7.5 Hz, 4H, CH$_2$CH$_3$), 4.28 (s, 3H, COOCH$_3$), 4.57 (q, J=7.5 Hz, 8H, CH$_2$CH$_3$), 8.72 (d, J=7.8 Hz, 2H, phenyl-H, meta to prophyrin), 8.90 (d, J=8.2 Hz, 2H, phenyl-H, ortho to porphyrin), 11.12 (s, 1H, monomethine bridge CH), 12.21 and 12.28 (2 d, J=13.5 Hz, each 2H, trimethine bridge CH=CHCH).

MS (EI, 70 eV): m/z (%)=720 (66) [M$^+$], 705 (16) [M$^+$—CH$_3$], 691 (36) [M$^+$—C$_2$H$_5$], 661 (8) [M$^+$—C$_2$H$_5$-2CH$_3$], 647 (10) [M$^+$—C$_2$H$_5$-3CH$_3$].

IR (KBr):ν=3034 cm$^{-1}$ (w, =CH), 2960, 2930 and 2870 (m, CH), 1725 (s, C=O), 1660 and 1590 (w, conjug. C=C), 1055, 1013, 950 (s).

UV/VIX (CH$_2$Cl$_2$): λ$_{max}$(1 g ε)=468 nm (5.390), 601 (4.118), 724 (3.347).

UV/VIS (CH$_2$Cl$_2$+1% TFA): λ$_{max}$ (1 g ε)=475 nm (5.694), 639 (4.186), 691 (3.927).

C$_{48}$H$_{54}$N$_4$.0.15 CHCl$_3$ (738.9) Calc. C 78.28, H 7.66, N 7.58, Found C 78.09, H 7.92, N 7.54.

We claim:

1. An azaporphyrin derivative of the formula I

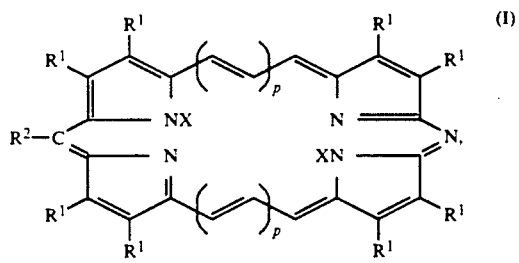

where

R$^1$ and R$^2$ are each independently of one another, hydrogen, unsubstituted C$_1$-C$_{20}$-alkyl, C$_1$-C$_{20}$-alkyl substituted with phenyl or C$_1$-C$_{12}$-alkoxycarbonyl, C$_5$-C$_7$-cycloalkyl, unsubstituted phenyl or phenyl substituted with halogen, cyano, C$_1$-C$_4$-alkyl, C$_1$-C$_4$-alkoxy, nitro or C$_1$-C$_4$-alkoxycarbonyl, or two adjacent R$^1$ radicals form, together with the carbon atoms to which they are bonded, an unsaturated or aromatic 5- to 7-membered carbocyclic ring, the X radicals are each independently of one another, hydrogen or C$_1$-C$_4$-alkyl, and p are each, independently of one another, 1 or 2.

2. An azaporphyrin derivative as claimed in claim 1, wherein R$^1$ and R$^2$ are each, independently of one another, hydrogen, unsubstituted or phenyl- or C$_1$-C$_4$-alkoxycarbonyl-substituted C$_1$-C$_4$-alkyl, or phenyl and the X radicals are each, independently of one another, hydrogen, methyl or ethyl.

* * * * *